United States Patent [19]

Lohse et al.

[11] 4,433,179
[45] Feb. 21, 1984

[54] PROCESS FOR THE PREPARATION OF DI- AND POLY-ALLYL ETHERS

[75] Inventors: Friedrich Lohse, Oberwil; Charles E. Monnier, Basel, both of Switzerland

[73] Assignee: Ciba-Geigy Corporation, Ardsley, N.Y.

[21] Appl. No.: 293,810

[22] Filed: Aug. 17, 1981

[30] Foreign Application Priority Data

Aug. 25, 1980 [CH] Switzerland .................. 6386/80

[51] Int. Cl.$^3$ ............................................. C07C 41/16
[52] U.S. Cl. .................................... 568/664; 568/673; 568/662; 568/616; 568/640; 568/648; 568/589; 560/179; 548/312; 548/341
[58] Field of Search .............. 568/671, 673, 664, 662, 568/616, 640, 648, 589; 560/179

[56] References Cited

U.S. PATENT DOCUMENTS 3,824,295  7/1974  Gordon .............................. 568/671
3,840,605 10/1974  Gordon .............................. 568/671
3,914,320 10/1975  Gordon .......................... 568/671 X

OTHER PUBLICATIONS

"Tetrahedron Letter", No. 38, (1975), pp. 3251–3254.
Dehmlow, Angewandte Chemie, 89 (1977), 521–533.
Herriott et al., Tetrahedron Letters, (1972), No. 44, pp. 4521–4524.
McKillop et al., Tetrahedron, vol. 30 (1974), pp. 1379–1382.

*Primary Examiner*—Bernard Helfin
*Attorney, Agent, or Firm*—Harry Falber

[57] ABSTRACT

A process for the preparation of allyl ethers of the formula $$R-O-CH_2-CH=CH_2)_n$$

in which R and n are as defined in claim 1, by reacting hydroxy compounds of the formula $$R-OH)_n$$

with allyl chloride or allyl bromide by phase transfer catalysis, 0.8 to 5 mols of allyl chloride or allyl bromide, 1 to 6 mols of aqueous or solid sodium hydroxide and, as the phase transfer catalyst, 2 to 20 mol % of a quaternary ammonium salt, a quaternary ammonium base or a crown ether being employed per hydroxyl equivalent of the compound of the formula II, and the reaction being carried out in the temperature range from 20° to 100° C.

9 Claims, No Drawings

PROCESS FOR THE PREPARATION OF DI- AND POLY-ALLYL ETHERS

The present invention relates to a process for the preparation of allyl ethers by reacting di-hydroxy and poly-hydroxy compounds containing an aliphatic, araliphatic, cycloaliphatic, cycloaliphatic-aliphatic or heterocyclic-aliphatic radical with allyl chloride or allyl bromide under conditions of phase transfer catalysis.

As is known, allyl ethers of aliphatic alcohols can be prepared in a simple manner from alkali metal alcoholates and allyl halides by the Williamson ether synthesis. However, the preparation of alcoholates of high-molecular alcohols, in particular of secondary and tertiary alcohols, frequently causes difficulties, since these alcohols do not readily react with, for example, sodium.

"Tetrahedron Letters", No. 38 (1975), pages 3251–3254, shows that asymmetrical ethers are obtained in high yields in an improved Williamson ether synthesis by applying phase transfer catalysts. This publication, however, does not indicate at any place that, if polyhydric alcohols, in particular polyhydric secondary or tertiary alcohols, are used, phase transfer catalysis leads to a high degree of allylation of all the hydroxyl groups of the polyhydric alcohol.

"Angewandte Chemie", 89 (1977), pages 521 to 533, where a report on the mechanism of phase transfer catalysis and on advances in phase transfer catalysis is given, also does not give any indication relating to the preparation of allyl ethers or polyhydric alcohols.

It has now been found that reaction products having a high degree of allylation are obtained in high yields by reacting polyhydric alcohols with allyl chloride or allyl bromide under conditions of phase transfer catalysis.

The present invention thus relates to a process for the preparation of allyl ethers of the formula I

$$R-O-CH_2-CH=CH_2)_n \quad (I)$$

in which R is an n-valent aliphatic, araliphatic, cycloaliphatic, cycloaliphatic-aliphatic or heterocyclic-aliphatic radical and n is a number of at least 2, by reacting hydroxy compounds of the formula II

$$R-OH)_n \quad (II)$$

in which R and n are as defined in formula I and the OH groups are bonded to primary, secondary or tertiary aliphatic C atoms, with allyl chloride or allyl bromide in the presence of a catalyst and in an alkaline medium, which process comprises carrying out the reaction by means of phase transfer catalysis, 0.8 to 5 mols of allyl chloride or allyl bromide, 1 to 6 mols of aqueous or solid sodium hydroxide and, as the phase transfer catalyst, 2 to 20 mol % of a quaternary ammonium salt, a quaternary ammonium base or a crown ether being employed per hydroxyl equivalent of the compound of the formula II, and the reaction being carried out in the temperature range from 20° to 100° C.

Preferably, hydroxy compounds of the formula II are employed, in which R is an n-valent aliphatic, araliphatic, cycloaliphatic, cycloaliphatic-aliphatic or heterocyclic-aliphatic radical having up to 120 C. atoms and n is a number from 2 to 6.

Especially, primary or secondary alcohols are used as the hydroxy compound of the formula II in the process according to the invention.

The starting materials for the preparation of the allyl ethers of the formula I are known compounds and are preferably employed in such quantities that the reaction mixture contains 0.9 to 2.5 mols of allyl chloride or allyl bromide per hydroxyl equivalent of the compound of the formula II. In particular, the starting materials are employed in equivalent quantities.

The conversion reaction can be carried out in the presence of either solid NaOH or aqueous NaOH solutions. As a rule, 20 to 99% aqueous NaOH solutions, preferably 30 to 80% solutions and in particular a 50% aqueous NaOH solution are used.

Moreover, the conversion reaction is preferably carried out in the temperature range from 25° to 80° C., in particular between 50° and 75° C.

Suitable dihydroxy compounds of the formula II are, for example: aliphatic diols, such as ethylene glycol, propane-1,3-diol, propane-1,2-diol, neopentyl glycol, butane-1,4-diol, butane-1,3-diol, hexane-1,6-diol, 2,2-diethylpropane-1,3-diol, 2-methyl-2-propyl-propane-1,3-diol, 2,2,4- or 2,4,4-trimethyl-hexane-1,6-diol, 2-methyl-2-ethyl-propane-1,3-diol, dodecane-1,12-diol or hydroxypivalic acid neopentyl glycol ester, unsaturated diols, such as butene-1,4-diol or butyne-1,4-diol, polyalkylene glycols, such as diethylene glycol, triethylene glycol or dipropylene glycol, and 1,4-bis-(hydroxymethyl)-benzene, the 1,4-bis-(hydroxyethyl ethers) of bisphenol A, bisphenol F or hydroquinone as araliphatic diols, and also cycloaliphatic and cycloaliphatic-aliphatic diols, such as cyclohexane-1,2-diol, cyclohexane-1,3-diol, cyclohexane-1,4-diol, hydrogenated bisphenol A or bisphenol F, 1,1-1,2-, 1,3- and 1,4-bis-(hydroxymethyl)-cyclohexane and the corresponding unsaturated cyclohexene derivatives, such as 1,1-bis-(hydroxymethyl)-cyclohexene and 1,4-bis-(hydroxymethyl)-cyclohexene, and heterocyclic-aliphatic diols, such as are obtained by adding 2 or more mols of an alkylene oxide, such as ethylene oxide, propylene oxide, butylene oxide, styrene oxide or cyclohexene oxide, in particular ethylene oxide, onto 1 mol of a mononuclear or polynuclear N-heterocyclic compound, such as hydantoin and its derivatives, dihydrouracil and its derivatives, barbituric acid and its derivatives, benzimidazolone and tetrahydrobenzimidazolone and derivatives thereof, bishydantoin and bis-dihydrouracil and derivatives thereof. Examples of compounds of this type are 1,3-di-(β-hydroxyethyl)-5,5-dimethylhydantoin, 1,3-di-(β-hydroxyethyl)-5-isopropylhydantoin, 1,3-di-(β-hydroxyethyl)-benzimidazolone, 1,3-di-(β-hydroxyethyl)-tetrahydrobenzimidazolone and 1,1'-methylene-bis-(3-β-hydroxyethyl-5,5-dimethylhydantoin), and the long-chain diols containing a heterocyclic radical.

Examples of trihydroxy, tetrahydroxy, pentahydroxy and hexahydroxy compounds of the formula II are: 1,1,1-tri-(hydroxymethyl)-ethane, 1,1,1-tri-(hydroxymethyl)-propane, tri-(hydroxymethyl)-nitromethane, glycerol, hexane-1,2,6-triol, butane-1,2,4-triol and the adducts obtained by adding an alkylene oxide, in particular 1–3 mols of an alkylene oxide, such as ethylene oxide, propylene oxide, styrene oxide or cyclohexene oxide, in particular ethylene oxide, onto these triols, N-heterocyclic trihydroxy compounds, such as 1,3,5-tris-hydroxyethyl isocyanurate, and also pentaerythritol, erythritol, xylitol, arabitol, mannitol, sorbitol and di-pentaerythritol.

The polyhydroxy compounds used in the process according to the invention can also be polyvinyl alcohols, in particular those having a mean molecular weight of up to about 15,000.

The phase transfer catalysts employed in the process according to the invention can be quaternary ammonium salts, for example tetramethylammonium chloride, tetraethylammonium chloride, benzyltrimethylammonium chloride, benzyltrimethylammonium acetate, methyltriethylammonium chloride, tetrabutylammonium chloride or tetrabutylammonium sulfate, quaternary ammonium bases, such as benzyltrimethylammonium hydroxide, and also the crown ethers, for example 12-crown-4-ether (1,4,7,10-tetraoxa-cyclododecane), 15-crown-5-ether (1,4,7,10,13-pentaoxacyclopentadecane), 18-crown-6-ether, dibenzo-18-crown-6-ether, dibenzo-24-crown-8-ether, dibenzo-1,4-dioxa-8,12-diazacyclopentadeca-5,14-diene, dicyclohexano-18-crown-6-ether or dicyclohexano-24-crown-8-ether.

The abovementioned crown ethers are known compounds and are commercially available.

The majority of the compounds which can be prepared by the process according to the invention are known. As far as they are novel compounds, protection is herewith also claimed. In particular, the diallyl ethers of hydrogenated bisphenol A and hydrogenated bisphenol F have not yet been described in the literature.

The present invention thus also relates to allyl ethers of the formula I, in which R is a radical of the formulae

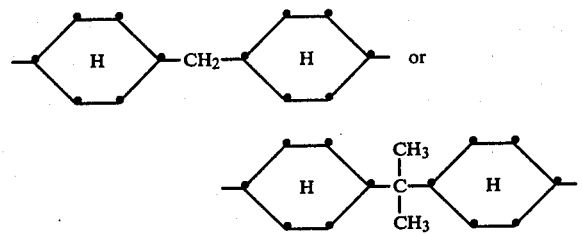

and n is the number 2, and to the mixture of the isomeric o,o-, o,p- and p,p-perhydrobisphenol F diallyl ethers.

The allyl ethers obtained by the process according to the invention are valuable monomers which, alone or as a mixture with other polymerisable monomers, for example diallyl phthalate, triallyl cyanurate or styrene, can be converted into crosslinked polymers. The allyl ethers obtained by the process according to the invention are also valuable starting materials for the preparation of epoxide compounds by the epoxidation process, halogen-free epoxide resins being obtained, in contrast to the preparation of epoxide resins by means of an epoxy-halogenohydrin.

General instructions for the preparation of allyl ethers 0.1 mol of a dihydroxy or polyhydroxy compound of the formula II, 0.1–0.6 mol of 50% aqueous NaOH, 0.25 mol of allyl chloride and 20 mol % of tetrabutylammonium bisulfate, relative to 1 hydroxy equivalent of alcohol, in 60 ml of an inert organic solvent, for example toluene or xylene, are introduced into a 0.3 l steel autoclave fitted with a magnetic stirrer. The mixture is warmed to 50°–55° C. and stirred for 5 hours at this temperature (about 1,000 revolutions per minute). Subsequently, the reaction mixture is stirred at 70°–75° C. for a further 15 hours. The reaction mixture is washed 3 times with 100 ml of water, and the organic phase is dried over sodium sulfate and concentrated. The crude product is distilled under a reduced pressure of about 0.13 mbar.

When preparing allyl ethers by the above working instructions, the use of an organic solvent can also be dispensed with.

EXAMPLE 1

64.0 g (0.27 mol) of perhydrobisphenol A (hydrogenated bisphenol A), 243.3 g (2.7 mols) of 50% aqueous NaOH, 204.0 g (2.7 mols) of allyl chloride and 36.3 g (0.11 mol) of tetrabutylammonium bisulfate in 160 ml of xylene are introduced into 1 liter steel autoclave. With vigorous stirring (about 1,000 revolutions per minute), the mixture is kept for 5 hours at 55°–60° C. and then for 15 hours at 70° C. After the reaction has ended, the reaction mixture is washed 3 times with about 200 ml of water, and the organic phase is dried over sodium sulfate and concentrated. This gives 81.13 g (93% of theory) of a yellowish resin of low viscosity. After distillation of the crude product at 159°–160° C./0.09 mbar, 73.11 g (86% of theory) of a colourless oil are obtained (content: 81.1% by weight of diallyl ether, 15.4% by weight of monoallyl ether and about 3.5% by weight of educt). Pure perhydrobisphenol A diallyl ether boils at 159°–160° C./0.11 mbar and is a colourless oil.

EXAMPLE 2

6.2 g (0.1 mol) of ethylene glycol, 40 g (0.5 mol) of 50% aqueous NaOH, 20 mol % of tetrabutylammonium bisulfate per hydroxyl equivalent of the glycol and 38 g (0.5) of allyl chloride in 60 ml of toluene are introduced into a 0.3 liter steel autoclave fitted with a magnetic stirrer. The mixture is heated with stirring at 50°–55° C. for 5 hours, and stirring is then continued for a further 15 hours at 70°–75° C. The reaction product is washed 3 times with 100 ml of water, and the organic phase is dried over sodium sulfate and concentrated. This gives 9.2 g of a colourless oil which is distilled at 110° C./33 mbar. Yield: 8.7 g (61% of theory) of ethylene glycol diallyl ether (purity >95%).

EXAMPLE 3

11.8 g (0.1 mol) of hexane-1,6-diol, 40 g (0.5 mol) of 50% aqueous NaOH, 20 mol % of tetrabutylammonium bisulfate per hydroxyl equivalent of the diol and 38 g (0.5 mol) of allyl chloride in 60 ml of toluene are introduced. The mixture is warmed at 80° C. for 15 hours. After working-up, 17.28 g (87% of theory) of a colourless oil are obtained which, after distillation at 90° C./0.04 mbar, gives 16.84 g (85% of theory) of colourless hexane 1,6-diallyl ether (purity >95%).

EXAMPLE 4

11.8 g (0.1 mol) of cyclohexane-1,4-diol, 40 g (0.5 mol) of 50% aqueous NaOH, 20 mol % of tetrabutylammonium bisulfate per hydroxyl equivalent of the diol and 38 g (0.5 mol) of allyl chloride are introduced. In accordance with Example 2, after a reaction time of 15 hours at 80° C., 14.11 g (72%) of colourless cyclohexane 1,4-diallyl ether are obtained, which is distilled at 110°–120° C./0.07 mbar and gives 13.45 g (69% of theory) of an allyl ether which consists of 94% by weight of cyclohexane 1,4-diallyl ether and 6% by weight of the monoallyl ether of cyclohexane-1,4-diol.

EXAMPLE 5

Under the conditions described in Example 2, 14.7 g (99% of theory) of pentaerythritol tetraallyl ether are obtained from 6.8 g (0.05 mol) of pentaerythritol and 38 g (0.5 mol) of allyl chloride; distillation of this product at 160° C./0.05 mbar gives 13.75 g (93% of theory) of pentaerythritol tetraallyl ether (purity ~99%).

EXAMPLE 6

In accordance with Example 2, 24.9 g (98% of theory) of trimethylolpropane allyl ether are obtained from 13.4 g (0.1 mol) of trimethylolpropane and 57 g (0.57 mol) of allyl chloride. After distillation at 120° C./0.08 mbar, this gives 23.55 g (93 of theory) of a trimethylolpropane allyl ether consisting of 79% by weight of trimethylolpropane triallyl ether and 21% by weight of trimethylolpropane diallyl ether.

EXAMPLE 7

As described in Example 2, 10.4 g (0.1 mol) of neopentyl glycol are reacted with 38 g (0.5 mol) of allyl chloride, 14.96 g (81% of theory) of neopentyl glycol allyl ether being obtained, which is distilled at 130° C./15 mbar and gives 14.4 g (78% of theory) of a neopentyl allyl ether consisting of 91% by weight of neopentyl diallyl ether and 9% by weight of neopentyl monoallyl ether.

EXAMPLE 8

(a) 482.5 g (2.28 mols) of a mixture of isomers of perhydrobisphenol F (about 10%/50%/30% o,o-/o,p-/p,p-), 480 g (12 mols) of sodium hydroxide pellets, 918 g(12 mols) of allyl chloride, 1,200 ml of toluene and 82 g (5 mol % per hydroxyl equivalent of the perhydrobisphenol F) of tetrabutylammonium bisulfate are introduced into a 6.3 liter steel autoclave. With vigorous stirring the mixture is warmed for 5 hours at 50° C. and then allowed to react for a further 15 hours at 80° C. After the reaction has ended, the reaction mixture is washed 3 times with about 1 liter of water and is concentrated in vacuo. This gives 558.3 g (84% of theory) of slightly yellowish perhydrobisphenol F diallyl ether. Distillation at 130°–135° C./0.13 mbar gives 355.6 g of pure colourless perhydrobisphenol F diallyl ether.

(b) 643.4 g (2.2 mols) of the perhydrobisphenol F diallyl ether obtained above and 241.5 g (5.25 mols) of formic acid in 2,500 ml of chlorobenzene are introduced into a 4.5 liter sulfonation flask fitted with a stirrer, thermometer, condenser and dropping funnel. The the course of about one hour, 510 g (10.5 mols) of 70% hydrogen peroxide solution are added dropwise to the mixture at 45°–50° C. Stirring is continued for a further 6 hours at 50°–55° C. After the reaction has ended, the organic phase is washed with sodium bisulfite until free from peroxide, and is then washed with water, dried over sodium sulfate and concentrated in vacuo. This gives 661.8 g (93% of theory) of a slightly viscous, colourless perhydrobisphenol F diglycidyl ether having an epoxide content of 4.91 equivalents/kg (theory 6.16 equivalents/kg). The product has a viscosity of 275 mPa.s at 25° C.

EXAMPLE 9

In place of tetrabutylammonium bisulfate according to Example 1, 18-crown-6-ether is used as the phase transfer catalyst.

12.0 g (0.037 mol) of perhydrobisphenol A, 20.0 g of powdered sodium hydroxide 0.53 g of 18-crown-6-ether (2mol % per hydroxyl equivalent) and 60 ml of toluene are warmed to 60° C. in a 200 ml sulfonation flask fitted with a stirrer, condenser, thermometer and dropping funnel. In the course of one hour, 18.15 g (0.15 mol) of allyl bromide are added dropwise at 70° C. The reaction mixture is stirred for 20 hours at 70° C., 200 ml of water are then added to the mixture and the aqueous phase is separated off. The organic phase is washed with 200 ml of 5% hydrochloric acid, dried over $Na_2SO_4$ and concentrated. This gives 13.51 g (84.3% of theory) of a slightly yellowish, viscous oil of the following composition: 53% by weight of diallyl ether, 31% by weight of monoallyl ether and 11% by weight of unconverted perhydrobisphenol A.

EXAMPLE 10

96 g (0.4 mol) of perhydrobisphenol A (hydrogenated bisphenol A), 80g (2.0 mols) of sodium hydroxide pellets, 153 g (2.0 mols) of allyl chloride and 13.6 g of n-dodecyldimethylbenzylammonium chloride and 200 ml of toluene are introduced into a 1 liter steel autoclave. With vigorous stirring (about 1,000 revolutions per minute), the mixture is kept at 55°–60° C. for 5 hours and then at 80° C. for 15 hours. After the reaction has ended, the reaction mixture is washed 3 times with about 500 ml of water, and the organic phase is dried over sodium sulfate, filtered and concentrated in vacuo. This gives 123.5 g (96.34% of theory) of perhydrobisphenol A diallyl ether (purity>95%).

EXAMPLE 11

43.2 g (0.3 mol) of 1,4-bis-(hydroxymethyl)cyclohexane, 120 g (3.0 mols) of powdered sodium hydroxide, 20.4 g of tetrabutylammonium bisulfate (10 mol % per hydroxyl equivalent) and 180 of toluene are introduced into a 750 ml sulfonation flask fitted with a stirrer, condenser, thermometer and dropping funnel. The mixture is warmed to 70° C., and 181.5 g (1.5 mols) of allyl bromide are added dropwise in the course of about one hour. Stirring is continued for 12 hours at 80° C. After the reaction has ended, the reaction mixture is washed with 200 ml of 5% hydrochloric acid solution and 700 ml of water. The organic phase is dried over $Na_2SO_4$ and concentrated. This gives 61.1 g (90.64% of theory) of slightly viscous 1,4-bis-(2-hydroxymethyl)-cyclohexane diallyl ether which, according to gas chromatography, is a single compound.

EXAMPLE 12

41.4 g (0.3 mol) of xylylene glycol, 120 g (3.0 mols) of sodium hydroxide, 20.4 g of tetrabutylammonium bisulfate (10 mol % per hydroxyl equivalent) and 180 of toluene are introduced into a 750 ml sulfonation flask fitted with a stirrer, thermometer, condenser and dropping funnel. The mixture is warmed to 70° C. Subsequently, 181.5 g (1.5 mols) of allyl bromide are added dropwise in the course of one hour. The reaction mixture is stirred for a further 12 hours at 82°–84 C. After the reaction has ended, the reaction mixture is washed successively with 500 ml of water, 300 ml of 5% hydrochloric acid solution and 300 ml of water. The organic phase is dried over sodium sulfate and concentrated, 64.43 g (98% of theory) of a slightly yellowish oil being obtained which, according to gas chromatography, is a single compound namely xylylene glycol diallyl ether.

EXAMPLE 13

7.6 g (0.05 mol) of xylitol, 100 g of 50% sodium hydroxide solution and 5 mol %, per hydroxyl equivalent of the xylitol, of tetrabutylammonium bisulfate in 60 ml of toluene are introduced into a 350 ml sulfonation flask fitted with a thermometer, stirrer and dropping funnel. The mixture is warmed to 70°–75° C. and 78 g of allyl bromide (0.625 mol) are added dropwise, with vigorous stirring. After a reaction time of 16 hours, the aqueous phase of the reaction mixture is separated off and the organic phase is washed 3 times with 70 ml of water, dried over sodium sulfate and concentrated. This gives 11.81 g of a slightly brownish oil which is distilled at 180°–200° C./0.03 mbar, 9.40 g (53% of theory) of a colourless oil being obtained (purity>98%).

EXAMPLE 14

4.55 g (0.025 mol) of D-sorbitol, 5.2 g of tetrabutylammonium bisulfate (10 mol % per hydroxyl equivalent) and 100 ml of 50 sodium hydroxide solution in 30 ml of toluene are introduced, as described in the preceding Example. The mixture is warmed to about 75°C. and 90.05 g (0.75 mol) of allyl bromide are added dropwise, with vigorous stirring, in the course of about 30 minutes. The reaction mixture is stirred for a further 16 hours at 75° C. After the reaction has ended, the aqueous phase is separated off and the organic phase is washed 3 times with 70 ml of water, dried over sodium sulfate and concentrated. 9.70 g (92% of theory) of a yellowish oil are obtained which, after distillation at 180°–200° C./0.01 mbar, gives 8.45 g (86.17% of theory) of sorbitol hexaallyl ether (purity>98%).

EXAMPLE 15

4.55 g (0.025 mol) of mannitol, 100 ml of 50% sodium hydroxide solution and 10 mol %, per hydroxyl equivalent of the mannitol, of tetrabutylammonium bisulfite in 30 ml of toluene are introduced. The mixture is warmed to 75°–80° C. and 90.05 g (0.75 mol) of allyl bromide are added dropwise, with vigorous stirring, in the course of 30 minutes. The reaction mixture is stirred at this temperature for 14 hours. After the reaction has ended, the aqueous phase is separated off and the organic phase is washed 3 times with about 70 ml of water, dried over sodium sulfate and concentrated. After distillation in a bulb tube at 50°–170° C./0.04 mbar, 8.75 g (83% of theory) of mannitol hexaallyl ether are obtained as a colourless liquid (purity>98%).

EXAMPLE 16

8.7 g (0.2 OH equivalents) of polyvinyl alcohol (mean molecular weight 2,000), 80 g (1 mol) of 50% sodium hydroxide solution, 39 g (0.5 mol) of allyl chloride, 6.8 g of tetrabutylammonium bisulfate (10 mol % per hydroxyl equivalent of the alcohol) and 60 ml of toluene are introduced into a 0.3 liter steel autoclave. With vigorous stirring (about 1,000 revolutions per minute), the mixture is warmed at 75°–85° C. for 24 hours. After the reaction has ended, the reaction mixture is washed with 4 times 100 ml of water, and the organic phase is dried over sodium sulfate, filtered and concentrated. This gives 13.4 g (79.7% of theory) of a clear, highly viscous resin which contains 9.3 double bonds/kg (78% of theory).

EXAMPLE 17

8.7 g (0.2 OH equivalents) of polyvinyl alcohol (mean molecular weight 14,000), 80 g (1.0 mol) of 50% sodium hydroxide solution, 7.8 g of tetrabutylammonium bisulfate (10 mol % per hydroxyl equivalent of the alcohol) and 60 ml of toluene are introduced into a 350 ml sulfonation flask. The reaction mixture is warmed to 65°–75° C. and, with vigorous stirring, 60.5 g (0.5 mol) of allyl bromide are added dropwise in the course of about 60 minutes. The reaction mixture is stirred for a further 24 hours. After the reaction has ended, the organic phase is washed with 3 times 100 ml of water, dried over sodium sulfate, filtered and concentrated in vacuo. 10.21 g of a brown resin (61.14% of theory) are obtained which contains 7.4 double bonds/kg (62% of theory).

What is claimed is:

1. A process for the preparation of an allyl ether of the formula I $$R—(O—CH_2—CH=CH_2)_n \quad \text{(I)}$$

in which R is an n-valent aliphatic, araliphatic, cycloaliphatic or cycloaliphatic-aliphatic radical and n is a number of at least 2, by reacting a hydroxy compound of the formula II $$R—(OH)_n \quad \text{(II)}$$

in which R and n are as defined in formula I and the OH groups are bonded to primary or secondary aliphatic C atoms, with allyl chloride or allyl bromide in the presence of a catalyst and in an alkaline medium, which comprises carrying out the reaction by means of phase transfer catalysis, 0.8 to 5 mols of allyl chloride or allyl bromide, 1 to 6 mols of aqueous or solid sodium hydroxide and, as the phase transfer catalyst, 2 to 20 mol % of a quaternary ammonium salt, a quaternary ammonium base or a crown ether being employed per one hydroxyl equivalent of the compound of the formula II, and the reaction being carried out in the temperature range from 20 to 100° C.

2. A process according to claim 1, wherein a hydroxy compound of the formula II is employed, in which R is an n-valent aliphatic, araliphatic, cycloaliphatic or cycloaliphatic-aliphatic radical having up to 120° C. atoms and n is a number from 2 to 6.

3. A process according to claim 1, wherein 0.9 to 2.5 mols of allyl chloride or allyl bromide are used per hydroxyl equivalent of the compound of the formula II.

4. A process according to claim 1, wherein the reaction is carried out in the presence of a 20 to 99% aqueous NaOH solution.

5. A process according to claim 1, wherein the reaction is carried out in the presence of a 30 to 80% aqueous NaOH solution.

6. A process according to claim 1, wherein the reaction is carried out in the temperature range from 25 to 80° C.

7. A process according to claim 1, wherein the reaction is carried out in the temperature range from 50 to 75° C.

8. An allyl ether of the formula I $$R(OCH_2CH=CH_2)_n \quad \text{(I)}$$

wherein R is a radical of the formulae

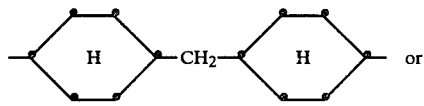 or
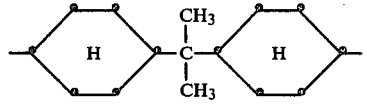
and n is the number 2.
9. A mixture of the isomeric o,o-, o,p- and p,p- perhydrobisphenol F diallyl ethers.
* * * * *